United States Patent [19]
Kaye et al.

[11] 4,022,416
[45] May 10, 1977

[54] PLASTIC BAND AND BAIL SYSTEM FOR INTRAVENOUS SOLUTION BOTTLES

[75] Inventors: Saul Kaye, Evanston; William G. Whitney, Skokie, both of Ill.

[73] Assignee: W. G. Whitney Corporation, Skokie, Ill.

[22] Filed: Oct. 29, 1975

[21] Appl. No.: 626,652

[52] U.S. Cl. .............................. 248/318; 24/73 R; 24/256
[51] Int. Cl.² .................. A44B 21/00; B42F 13/00
[58] Field of Search ................... 24/256, 257 R, 73; 220/94 R; 248/359, 318

[56] References Cited
UNITED STATES PATENTS

| | | | |
|---|---|---|---|
| 232,925 | 10/1880 | Betts | 24/256 |
| 3,807,679 | 4/1974 | Burke et al. | 24/256 |

*Primary Examiner*—Werner H. Schroeder
*Assistant Examiner*—Doris L. Troutman
*Attorney, Agent, or Firm*—Hill, Gross, Simpson, Van Santen, Steadman, Chiara & Simpson

[57] ABSTRACT

A plastic band and bail system to be attached to bottles containing solutions for intravenous administration, wherein a plastic band surrounds the bottle and a bail of plastic material is formed integral with or attached to the plastic band.

10 Claims, 12 Drawing Figures

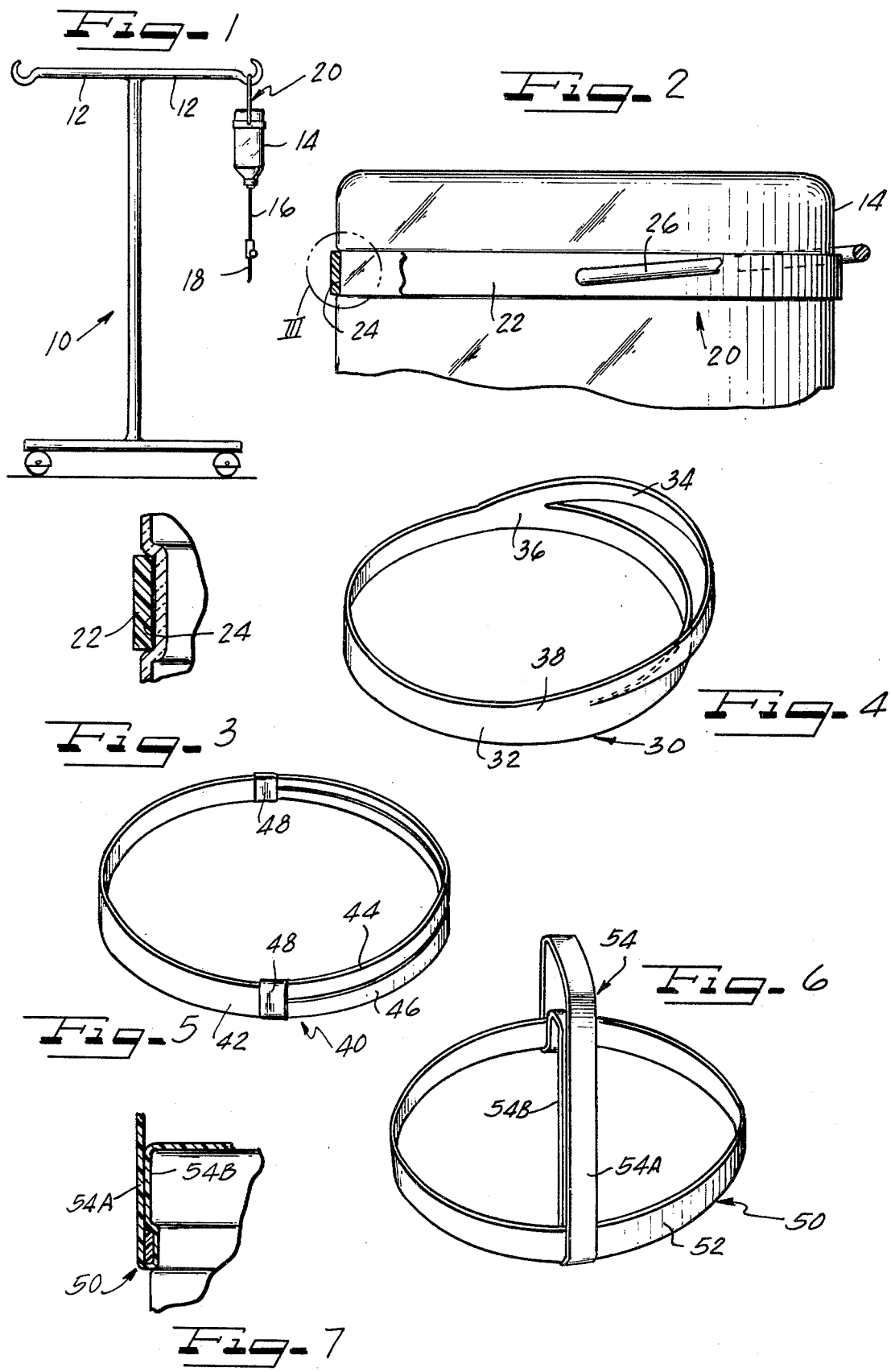

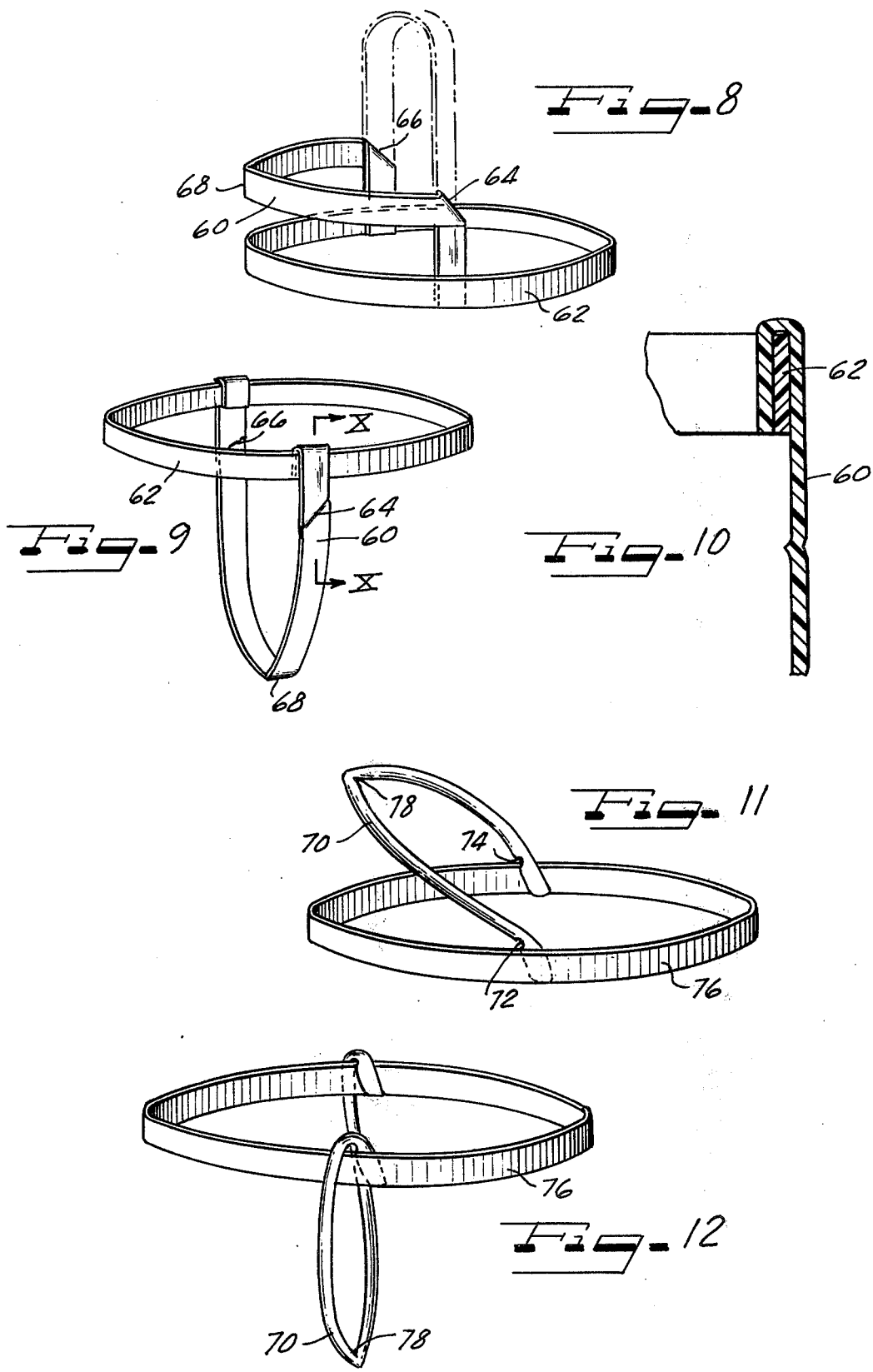

4,022,416

PLASTIC BAND AND BAIL SYSTEM FOR INTRAVENOUS SOLUTION BOTTLES

This invention relates to a plastic band and bail system for suspending bottles containing intravenous solutions, during administration.

Solutions are often administered intravenously from a glass bottle through plastic tubing and a needle attached to the plastic tubing, into a patient's vein. The solution obtains its pressure by gravity feed as the bottle is hung neck down with a hanger or bail, which is affixed to a band located in a special groove molded into the wall of the glass bottle, near the base. These bails and bands have been made of metal, and this construction presents certain disadvantages. In the first place, they are relatively expensive. Furthermore, they sometimes rust, which makes for a somewhat unsanitary condition. In addition, the metal bands sometimes become dislodged from the bottle because the clip which holds them on the bottle can be easily opened. Therefore, it has become desirable to develop a band and bail system which overcomes these disadvantages.

SUMMARY OF THE INVENTION

It is an object of the present invention to provide an intravenous solution bottle with a plastic band and bail system attached thereto which is tightly secured to the bottle, minimizing breakage and which is also readily applied to the bottle during the processing of the intravenous solution.

It is a further object to provide a plastic band and bail system for attachment to an intravenous solution bottle which is economical and relatively easy to manufacture.

Another object is to provide a bail system for attachment to an intravenous bottle which is not subject to rusting.

It is another object of the invention to provide a band and bail system for attachment to an intravenous bottle which will remain in position around the bottle during storage but in which the bail member will flex easily to a position ready for use.

By way of summary, the invention herein provides a plastic band and bail system which is easy to manufacture and is economical. It comprises generally a band and bail which is slipped over an I.V. bottle with the band sitting in the preformed groove which is a characteristic of such bottles molded around the wall of the bottle, near the base. During the manufacturing process, I.V. solutions are sterilized by exposure to steam under pressure (autoclaving). The bail-band may be placed on the bottle before it is autoclaved, and then, during this heating process the band of plastic material shrinks circumferentially at a controlled rate to the proper final length. At the completion of the autoclaving the band fits tightly around the base and the bail is positioned so that it can be moved into the proper position ready for hanging the bottle. As an alternative, it may be desirable to place the band on the bottle after autoclaving and then heat shrinking the band onto the bottle by a subsequent heating process using either a ring heater or a blast of hot air, for example.

Other objects and advantages of the invention will become more readily apparent when considering the following description in connection with the drawings.

BRIEF DESCRIPTION OF THE DRAWINGS

FIG. 1 illustrates a stand used in a hospital for hanging an intravenous feeding bottle therefrom;

FIG. 2 is a view in elevation illustrating the base of a bottle in an inverted position and incorporating a plastic band and bail system according to the present invention;

FIG. 3 is an enlarged view of the circled portion of FIG. 2 showing a plastic band fitted into a groove in the base of the bottle;

FIG. 4 is a perspective view of a modified construction of a plastic bail and band for attachment to an intravenous bottle;

FIG. 5 is another modification of a plastic bail and band for attachment to an intravenous bottle;

FIG. 6 is a perspective view of another modification of a bail and band for attachment to an intravenous bottle;

FIG. 7 is a partial view in elevation illustrating attachment of the plastic bail and band of FIG. 6 to an intravenous bottle;

FIG. 8 is a perspective view of another modified construction of a plastic bail and band for attachment to an intravenous bottle;

FIG. 9 is a perspective view of the bail and band of FIG. 8 as it would appear when attached to an intravenous bottle ready to be put into a hanging position;

FIG. 10 is a section view taken along line X—X of FIG. 9;

FIG. 11 is a perspective view of still another modified construction of a plastic bail and band;

FIG. 12 is a perspective view of the bail and band of FIG. 11 as it would appear when attached to an intravenous bottle ready to be put into a hanging position.

DESCRIPTION OF PREFERRED EMBODIMENTS

Turning now to the drawings, there is shown in FIG. 1 a stand 10 of the type used for supporting intravenous solution bottles. The stand 10 may have support arms 12 from which an intravenous bottle 14 is hung in an inverted position so that solution is fed from the bottle through the tube 16 and a needle 18 to a patient. A bail and band system 20 attached to the bottle 14 is used to hang the bottle from the arm 12.

In FIG. 2 there is illustrated one form of the invention in which a plastic bail and band system 20 is attached to the bottle 14. The plastic bail and band system 20 comprises a plastic band 22 which is fitted in a groove 24 formed in the bottle 14. Affixed to the band 22 is a bail 26. It may be affixed to the band 22 by heat sealing. The bail 26 may be of a similar plastic material. Preferably it is affixed to the band 22 at any angle up to 90°. The band is of a shrinkable plastic material. Since upon heating the band 22 shrinks tightly onto the bottle into the groove 24, the bail member 26 should have a radius slightly larger than the band 22 so that when the bottle is hung from a stand 10, the bail 26 may be easily extended over the bottom of the bottle into a use position ready for hanging. It will be appreciated that while the radius should be large enough to permit of its being moved into a use position, it should not be so large that it is not firm against the side of the bottle when in a storage position.

FIG. 3 illustrates an enlarged partial sectional view of the band 22 in position in the groove 24 of the bottle after being shrunk into position.

The bail and band system 20 is constructed in such a size that it may easily be slipped over the end of an intravenous bottle to which it is to be attached and the band 22 fitted into groove 24. Then when the bottle is sterilized by the autoclaving process the band 22 controllably shrinks into a tight fitting position in the groove 24. The band 22 may also be attached to the bottle after sterilization of the latter, by heat shrinking into place by several different means such as, for example, by a ring heater or a blast of hot air.

FIG. 4 illustrates a modified version of a plastic bail and band system 30 which includes a band 32 and a bail 34. The band 32 is of substantially the same width throughout its circumference and is of a sufficient width to occupy substantially all of the groove 24 as shown in FIG. 3. The bail member 34 is integrally attached to the band 32 at substantially diametrically opposed positions 36 and 38. It will be observed that the bail member 34, which is in effect a second half loop, is disposed at an angle to the band 32, which may be on the order of 5°–10°. In addition, the bail 34 is of a slightly larger radius than the band 32 and is made so for the same reason as explained in connection with the bail member 26 shown in FIG. 2.

A further modified version 40 of a plastic bail and band system is shown in FIG. 5. This comprises a band 42 which is split horizontally for approximately half of its circumference to divide it into upper and lower portions 44 and 46. The lower portion 46 along with the remaining full width of the band 42 are positioned in a groove 24 of a bottle 14. The upper portion 44 is then used as the bail member. It will be noted that when the unit 40 is placed in the groove of a bottle it will be necessary to assure that the upper portion 44 is not placed in the groove so that it does not shrink into the groove during the shrinking process which secures the band 42 in the groove of the bottle. In this particular type of bail-band unit, reinforcing strips 48 are placed upon the band at the beginning of the slit 45 so that the slit does not progress further around the band.

FIGS. 6 and 7 illustrate another version of a bail and band system 50 wherein the band member and the bail member are separate units. The system includes a band member 52 which is shrunk onto the bottle in a groove 24 in a manner as previously described. The system also includes a separate loop of a plastic material which comprises the bail member 54. It will be observed from FIG. 7 that the loop has a portion 54A which extends downwardly and around the band 52 and then is turned upwardly into a portion 54B so as to completely surround the band 52. It will be observed, particularly from FIG. 7, that the bail member 54 is captured or held in place by the band 52 on the bottle 14. An important consideration in this particular embodiment is that the bail member must easily collapse against the bottom of the bottle so that it does not interfere with the normal storage and handling of the bottle. Furthermore, the bail member 54 should not be able to slide around the bottle to thereby exert an unbalanced force on the band, which might allow it to be pulled off the bottle when the bottle is hung in a use position.

Further modifications are illustrated in FIGS. 8 through 12. In FIG. 8 the flat strap bail 60 is sealed to the inside of the band 62 so that when it is folded down into the position for hanging, the bail is folded back on itself as seen in FIG. 10 for greater security and held tightly against the bottle by the shrinking action of the band.

Normally, if the strap bail is folded from the normal or storage position (FIG. 8) to the hanging position (FIG. 9) this action causes a half twist to occur in the bail which can cause a crease or fold to occur in the bail in the hanging position, thus causing the bottle to hang at an angle rather than vertical. To avoid this, a half twist is put into the bail by prefolding it on the creases 64 and 66 as shown in FIG. 9. Then when the bail is brought down into the hanging position, the creases unfold, eliminating the half twist.

To further assure the straight hanging of the bottle, a third crease 68 is formed in the center of the bail to help locate the bottle level in the hanger.

Instead of using a flat strap bail, a similar configuration can be accomplished with a tubular bail 70 as shown in FIGS. 11 and 12. However, instead of a crease at the side of the bail, a predetermined folding point is established by means of crimps 72 and 74 just above where the bail is sealed on the inside of the band 76. Note that the bail 70 is sealed at an angle on the band 76 to allow it to fit snugly against the side of the bottle in the storage position. Here again, a crease is formed in the center of the bail to assist in hanging the bottle level in the hanger.

In making any of the plastic bail-band systems shown herein, it is important that the material used be strong enough to withstand the force of handling. It should also have the property of being able to shrink circumferentially tightly around the bottle and retaining this tight configuration. Furthermore, the material must be subject to shrinkage in the proper temperature ranges through which the bottle is exposed during such a process as autoclaving. Examples of suitable materials that might be used for any of the bail-band systems illustrated are thermoplastics such as polypropylene, polypropylene copolymers, polyester, polyvinylchloride, nylon and high density polyethylene.

It will be apparent that the invention disclosed herein provides several embodiments of plastic bail and band systems which are simple in construction and easy to manufacture. Furthermore, they should be relatively inexpensive. In addition, they have the advantage of being more sanitary than metal systems, which are often subject to rusting.

While certain preferred embodiments of the invention have been disclosed, it will be appreciated that these have been shown by way of example only and the invention is not to be limited thereto as other variations probably will be apparent to those skilled in the art and the invention is to be given its fullest possible interpretation within the terms of the following claims.

What is claimed is:

1. A plastic bail and band system for attachment to an intravenous solution bottle, comprising:
    a plastic band attachable in a groove in a wall of the bottle near a base thereof, the band being made of a plastic which shrinks circumferentially upon heating to sterilizing temperatures; and
    a plastic bail member attached to said band at opposite ends of said member at substantially diametrically opposed positions on said band.
2. The bail and band system of claim 1 wherein the plastic bail member is a separate member.
3. The bail and band system of claim 1 wherein the plastic bail member is of a slightly larger radius than said band.
4. The bail and band system of claim 1 wherein said band is slit horizontally through approximately half its circumference into two parallel portions, one of said portions being a continuation of the band and the other of said portions being the bail.

5. The bail and band system of claim 4 including two substantially vertically extending strips positioned on said band at each end of said slit to prevent the slit from progressing further around the band.

6. The system of claim 1 wherein said band and bail members are separate members; and said bail comprises a loop extending vertically to said band and is held in position by said band when disposed on a bottle.

7. The bail and band system of claim 1 wherein said bail member comprises a flat strap member and includes
means defining a pair of creases in said bail member, each of the creases of said pair being spaced substantially equidistantly from the position of attachment of said bail member to said band, whereby when said bail member is extended to a bottle hanging position the bail member is disposed in an untwisted position.

8. The bail and band system of claim 1 wherein said bail member comprises a flat strap member, the ends of which are attached to the inside of said band so that when the system is attached to a bottle the bail member will be secured tightly to the bottle by the band.

9. An intravenous solution bottle for hanging in a dispensing position comprising:
means defining a circumferentially extending groove formed in the outer surface of the lower portion of the bottle;
a plastic bail and band system attached to the bottle and including,
a heat-shrinkable plastic band fitting tightly in said groove, and
a plastic bail member attached to said plastic band.

10. The device of claim 9 wherein
said bail member is a separate member from said band.

* * * * *